United States Patent
Zonneveld

[19]

[11] Patent Number: 5,889,611
[45] Date of Patent: Mar. 30, 1999

[54] OPERATING MICROSCOPE

[75] Inventor: Frans W. Zonneveld, Eindhoven, Netherlands

[73] Assignee: U.S. Philips Corporation, New York, N.Y.

[21] Appl. No.: 858,481

[22] Filed: May 16, 1997

Related U.S. Application Data

[63] Continuation of Ser. No. 410,020, Mar. 24, 1995, abandoned.

[30] Foreign Application Priority Data

Mar. 24, 1994 [EP] European Pat. Off. ............. 94200761

[51] Int. Cl.⁶ .......................... G02B 21/22; G02B 21/36
[52] U.S. Cl. ........................... 359/376; 359/368; 359/369
[58] Field of Search .................................. 359/368–390, 359/363, 630; 364/525, 555; 348/42, 44, 51, 77–79, 360; 351/212; 600/407, 310, 424, 427; 356/349, 372, 432; 128/898–923, 857; 345/419–429, 31, 139

[56] References Cited

U.S. PATENT DOCUMENTS

| | | | |
|---|---|---|---|
| 3,632,866 | 1/1972 | King ............................................ | 348/51 |
| 4,439,010 | 3/1984 | Doty ........................................... | 359/630 |
| 4,643,540 | 2/1987 | Kawasaki et al. ....................... | 359/368 |
| 4,720,804 | 1/1988 | Moore ....................................... | 359/368 |
| 4,722,056 | 1/1988 | Roberts et al. .......................... | 364/413 |
| 4,786,154 | 11/1988 | Fantone et al. .......................... | 359/369 |
| 4,871,245 | 10/1989 | Ishikawa et al. ........................ | 359/363 |
| 4,987,488 | 1/1991 | Berci ......................................... | 348/77 |
| 5,276,550 | 1/1994 | Kojima ..................................... | 359/383 |
| 5,416,633 | 5/1995 | Michel et al. ........................... | 359/410 |

OTHER PUBLICATIONS

"A Frameless Stereotaxic Integration Of Computerized Tomographic Imaging And The Operating Microscope" Journal of Neurosurgery 65 (1986) pp. 545–549.

Watanabe et al., "Three–Dimensional Digitizer (Neuronavigator):New Equipment for Computed Tomagraphy–Guided Stereotaxic Surgery", Surg Neurol 1987;27;543–7.

*Primary Examiner*—Thong Nguyen
*Attorney, Agent, or Firm*—Dwight H. Renfrew, Jr.

[57] ABSTRACT

The invention provides an operating microscope for observing an operating field and also for producing a three-dimensional visualization of image data of the operating field or also of a vicinity of the operating field. The user of the operating microscope, for example a surgeon, can observe a three-dimensional visualization of image data during use of the operating microscope, said image data having been acquired by computerized tomography (CT) or magnetic resonance imaging (MRI) and being stored in an image memory. Preferably, an image processing unit derives a stereoscopic image of the operating field from the stored image data, which stereoscopic image is coupled into the binocular of the operating microscope. The user can then optionally observe the actual operating field or a perspective image formed by means of the registered image data. The operating microscope comprises a system of position sensors for determining the setting of the operating microscope and for applying the setting to the image processing unit so that a stereoscopic image is formed with settings, such as viewing angle and magnification, corresponding to the setting of the operating microscope.

20 Claims, 1 Drawing Sheet

OPERATING MICROSCOPE

This is a continuation of application Ser. No. 08/410,020, filed Mar. 24, 1995, now abandoned.

BACKGROUND OF THE INVENTION

1. Field of the Invention

The invention relates to an operating microscope for observing an operating field, which includes an image display device for displaying an image derived from registered image data, and an optical system for combining the derived image with the observation of the operating field.

2. Description of the Related Art

An operating microscope of this kind is known from the article "A frameless stereotaxic integration of computerized tomographic imaging and the operating microscope" in Journal of Neurosurgery 65 (1986), pp. 545–549.

The known operating microscope comprises an imaging device which includes a miniature black and white display screen on which a contour of a relevant part of the operating field is displayed. The imaging device also comprises a beam splitter whereby the contour displayed on the miniature display screen and the actual operating field are simultaneously visualized for the user of the operating microscope. Using an arithmetic device, the contour of the relevant part, for example a tumor to be removed, in the operating field is derived from image data (CT data) previously registered by means of an X-ray computerized tomography device. A drawback of the known operating microscope consists in that during observation of the actual operating field only a limited image data visualization, containing two-dimensional information, is available to the user.

For projection of the contour derived from the CT data it is necessary to register the CT data and the optical axis of the microscope in a common coordinate system. From the cited article it is known to provide fiducial markers on the patient to be examined for this purpose. The markers are non-transparent to X-rays and are taken up in the CT data. The position of the operating microscope is determined by means of a three-dimensional acoustic referencing system which utilizes an acoustic localizer which generates ultrasonic pulses in a spark gap of a spark plug attached to the operating microscope. The ultrasonic pulses are picked up by three microphones which are mounted on a stand and which determine the coordinate system in the operating room. At the beginning of an operation the operating microscope is successively directed to the markers and the successive positions of the operating microscope are registered in the coordinate system by the acoustic localizer. For a new setting of the operating microscope, involving selection of a new focal plane, the position of the operating microscope should again be determined by means of the acoustic referencing system. From the CT data there are subsequently derived image data which correspond to a slice of the patient in the focal plane whereto the operating microscope is adjusted, and from these image data a contour of relevant structures, for example a tumor, is derived.

SUMMARY OF THE INVENTION

It is inter alia an object of the invention to provide an operating microscope which offers access to as much information as possible from recorded image data of the operating field, or also of a vicinity of the operating field, during use.

To this end, an operating microscope according to the invention is characterized in that the optical system comprises means for spatially visualizing the derived image in a manner corresponding to a spatial observation of the operating field.

The user of an operating microscope according to the invention has access to three-dimensional information from image data relating to the operating field or also to a vicinity of the operating field. The image data have been registered, for example prior to an operation, by way of an imaging means such as an X-ray computerized tomography (CT) device or a magnetic resonance imaging (MRI) device. The user, for example the surgeon or his/her assistant observes the operating field via the operating microscope, but can also compare the operating field observed with a visualization of the same field obtained from the registered image data. The visualization contains three-dimensional image information and takes into account the viewing angle and the depth with which the actual operating field is observed by the operating microscope. It is thus achieved notably that the display of the three-dimensional image information and the observation of the operating field register as well as possible. The visualization of the three-dimensional image data may constitute a complete three-dimensional image in which directions, distances and orientations are visible. The visualization of the three-dimensional image data may also be a partly three-dimensional representation with directions and orientations but without spacings; such a representation is sometimes referred to as a 2½-dimensional image.

The image data can be visualized, for example by means of one or more miniature display tubes. The dimensions of the display tubes are preferably as small as possible so as to keep the dimensions of the operating microscope according to the invention acceptably small, thus enabling flexible use during an operation. Color LCD display screens can also be used for the visualization of the image data.

Because a visualization of three-dimensional image information is available in combination with a view of the actual operating field, the user of the operating microscope has a better and more direct view with more information of the operating field, because the user sees the visualization of the image data and the operating field three-dimensionally in about the same way. The user of the operating microscope thus has access to three-dimensional information which contains treatment-supporting information, without it being necessary to interrupt the use of the operating microscope. The treatment-supporting information includes, for example an image of the operating field in which pathologic and normal morphologies are visualized in a suitably distinct manner. If desired, the user of the operating microscope also has access to a visualization of a vicinity of the actual operating field. The user can thus more readily make a decision as regards the justified and/or effective continuation of a medical intervention such as an operation.

A further preferred embodiment of an operating microscope according to the invention is characterized in that the visualization of image data constitutes a stereoscopic image.

The visualization of three-dimensional information in the form of a stereoscopic image offers the advantage that the user of the operating microscope sees the visualization of image data with depth. The image data are preferably visualized in conformity with the setting of the operating microscope for the observation of the actual operating field. The visualization of the three-dimensional image data then spatially registers as well as possible with the image of the actual operating field. Visualization in the form of a stereoscopic image offers the advantage that the user of the operating microscope can compare information from the registered image data directly with the observation of the actual operating field, without it being necessary for the user of the operating microscope to interpret the visualization of the image data.

A further preferred embodiment of an operating microscope according to the invention comprises a binocular with a left channel and a right channel and is characterized in that a left image of the image data visualization is reproduced in the left channel and a right image is reproduced in the right channel, the left image and the right image together constituting the stereoscopic image.

An operating microscope according to the invention which comprises a binocular can visualize the stereoscopic image by means of a comparatively simple construction. From the image data there are derived a left image and a right image, i.e. the left image and the right image visualize image data corresponding to the operating field, or also to a vicinity thereof, as seen by the user's left eye and right eye, respectively. The images are displayed in the left channel and the right channel of the binocular operating microscope. The user of the operating microscope then observes a stereoscopic image with depth which is composed from the image data previously registered by an imaging means.

It is also an object of the invention to provide an operating microscope which keeps the visualization of image data with three-dimensional information in conformity with the setting of the operating microscope.

A further preferred embodiment of an operating microscope according to the invention is characterized in that the operating microscope comprises at least one position sensor for applying at least one electronic position signal to a converter for deriving a variable setting of the operating microscope and for applying an adjustment signal, corresponding to the setting, to an image processing unit for processing the image data for visualization in conformity with the setting of the operating microscope.

In order to compare the three-dimensional visualization, for example in the form of a stereoscopic image, with the observation of the actual operating field, the three-dimensional information is preferably visualized in conformity with the setting of the operating microscope. Preferably, the microscope viewing angle, magnification and perspective of observation of the actual operating field are the same as used to visualize the three-dimensional image data. To this end, the image data are visualized in the same coordinate system as the actual operating field. In order to register the setting of the operating microscope and to determine said coordinate system, one or more position sensors are provided. The position sensors are provided, for example on the stand wherefrom the operating microscope is suspended and also on an adjusting mechanism for the objective lens whereby the magnification is (also) adjusted. The position sensors are preferably constructed as potentiometers, because potentiometers do not cause sparks so that they can also be used in an operating room in which volatile, combustible substances are used for anesthesia. A converter converts the electronic signals supplied by the position sensors into adjustment signals which represent the viewing direction, distance and or magnification settings of the operating microscope. The adjustment signals are applied, together with the image data, to an image processing unit in which they are processed so as to form a visualization corresponding to the setting of the operating microscope. If desired, the position sensors may also be activated during operation of the operating microscope in order to supply adjustment signals in response to a change of the setting of the operating microscope. The image processing unit keeps the visualization of the image data in conformity with the setting of the operating microscope by means of said adjustment signals.

A further preferred embodiment of an operating microscope according to the invention is characterized in that the operating microscope is provided with a control unit for forming a sectional plane through the image data by means of an image processing unit.

Such a sectional plane through the image data preferably corresponds to an adjusted focal plane of the operating microscope or to a plane in the adjusted depth of focus range of the operating microscope. Such a sectional plane is chosen by the user by means of a control unit which is coupled to the image processing unit, or which forms a part thereof, in order to adjust the image processing unit for the formation of a desired sectional plane. The sectional plane can also be derived from the adjustment signals by the image processing unit. When an sectional plane has been formed through the image data, the image data are further processed so as to obtain a visualization of the image data relating to structures situated to the other side of the sectional plane, viewed in the viewing direction of the user. For example, the image data can be processed in the image processing unit in such a manner that the image data of the structures present between the user and the sectional plane are visualized in a transparent manner; they can also be omitted from the visualization. It is thus achieved that the user has an unobstructed view of the structures at the level of the operating field, which view is not obscured by visualization of image data of structures present in zones between the user and the selected sectional plane.

A further preferred embodiment of an operating microscope according to the invention is characterized in that the operating microscope comprises an adjustable coupling device for selectively observing the operating field, the visualization of the image data, or simultaneously a composite image of the operating field and the visualization of the image data.

In order to enable easy comparison of the actual operating field and the visualization of image data of the operating field, or of a vicinity thereof, by the operating microscope according to the invention, the operating microscope can be switched between observation of the operating field and observation of the visualization of image data. The operating microscope is preferably constructed so that it can be switched by means of an adjustable coupling device. The coupling device combines the visualization of the image data with the visualization of the actual operating field. The coupling device is adjustable either to enable the user of the operating microscope to observe the operating field or to offer the user a visualization of image data, simultaneously with the observation of the actual operating field or not. As a result, the operating microscope enables the user either to view alternately the actual operating field or the visualization of image data for the operating field, or also a vicinity thereof, or to view an image of the actual operating field combined with the visualization of the image data.

A further preferred embodiment of an operating microscope according to the invention is characterized in that the coupling device comprises at least one movable mirror.

A comparatively simple and reliable construction of an adjustable coupling device is achieved by using one or more movable mirrors, or other reflectors. In a deflected position of such a movable mirror the user of the operating microscope can view the actual operating field, and in an active position such a mirror is adjusted so that the visualization of image data is mirrored into the optical path of the ocular section of the operating microscope so that it becomes visible to the user. The observation of the actual operating field in combination with the visualization of image data is made possible for the user by constructing the mirrors to be partly or semi-transparent.

BRIEF DESCRIPTION OF THE DRAWINGS

The invention will be described in detail hereinafter on the basis of an embodiment and the accompanying drawing; therein.

DETAILED DESCRIPTION OF THE PREFERRED EMBODIMENTS

Figure 1:
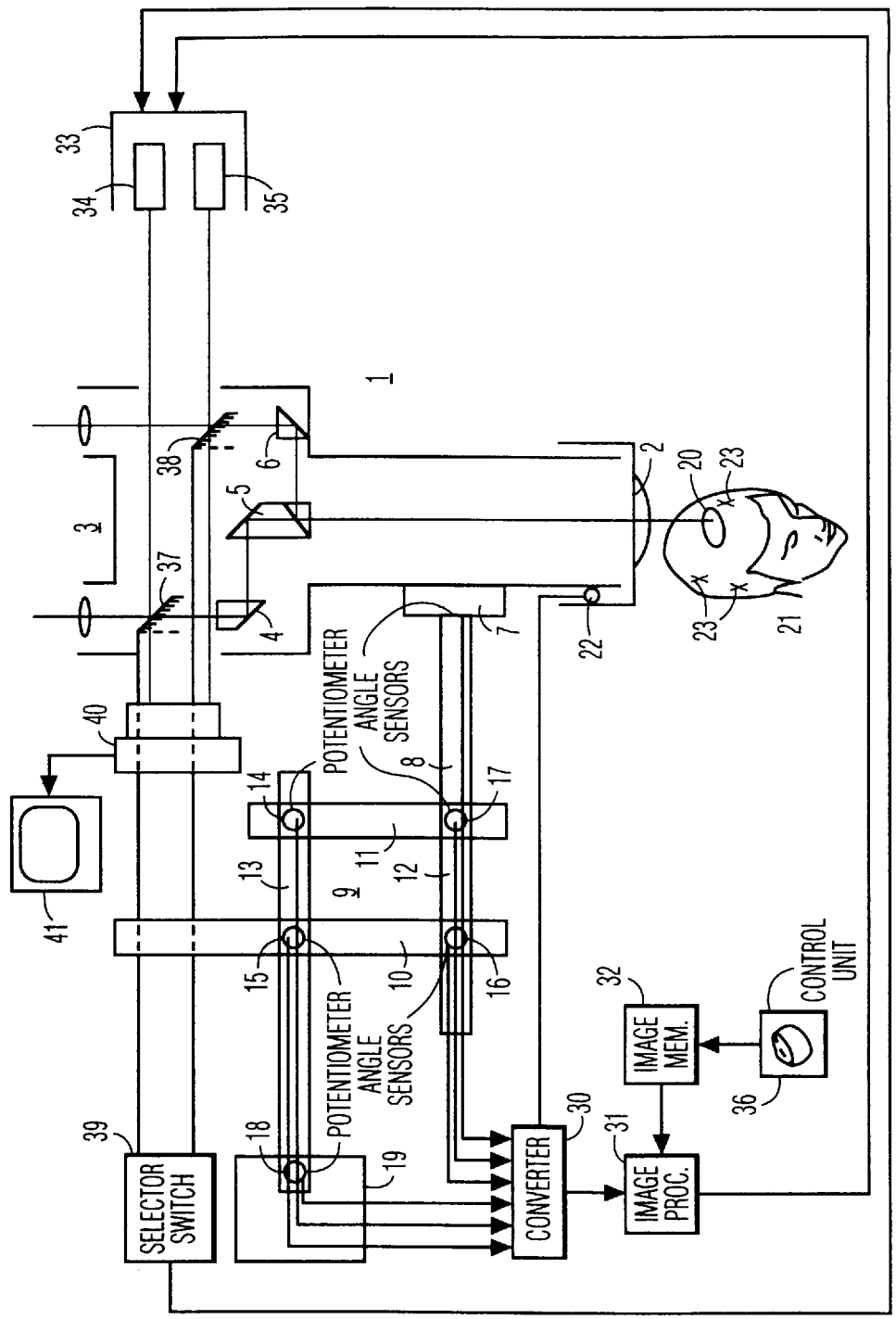
FIG. 1 shows diagrammatically an operating microscope according to the invention.

FIG. 1 is a diagrammatic representation of an operating microscope according to the invention. The operating microscope 1 comprises an adjustable objective lens 2 and binocular 3 with a set of prisms 4, 5 and 6. The operating microscope is connected, via a hinge 7, to a suspension arm 8 which forms part of a system of rods 9 which also comprises two parallel rods 10 and 11. The parallel rods are interconnected by connection members 12 and 13 which are connected to the respective parallel rods by way of pivots 14, 15, 16 and 17. The system of rods 9 is connected to a stand 19 by way of a further pivot 18. The operating microscope 1 can be displaced at random by means of the rod system and the suspension arm so as to be aimed at an operating field 20. In the present example the operating field is a part of the skull volume of a patient 21 undergoing brain surgery.

The pivots 14, 15, 16, 17 and 18 and the hinge 7 are provided with potentiometers. The potentiometers act as angular position sensors and apply electronic position signals to a converter 30 which derives the viewing direction of the operating microscope and the distance between the operating microscope and the operating field from the electronic position signals. The viewing direction is the angle at which the operating field 20 is observed by the operating microscope. The setting of the objective lens is converted, by means of a position sensor 22, into an adjustment signal which is also applied to the converter 30 which derives the adjusted magnification of the operating microscope therefrom. The viewing direction and the distance are also determined on the basis of fiducial markers 23 provided on the patient. In order to define positions in the three-dimensional space, at least three markers are provided on the patient; however, in order to enable tests to be carried out and adjustment errors to be avoided, preferably more than three markers are used.

Adjustment signals supplied by the converter and representing the viewing direction, the distance and the magnification settings are applied to an image processing unit 31. Three-dimensional image data of the patient 21 to be examined and/or treated are stored in an image memory 32. These image data have been acquired, for example by means of an imaging means (not shown) such as an X-ray computerized tomography device or a magnetic resonance imaging device. The markers provided on the patient are such that they are also visualized by the imaging means. On the basis of the adjustment signals and the image data, the image processing unit 31 forms an image signal for a stereoscopic image which corresponds to the operating field, or also to a vicinity thereof, and which visualizes the image data of the operating field, or also of a vicinity thereof with the same viewing direction, distance and magnification as used to observe the operating field itself. The stereoscopic image is visualized by a display unit 33 which comprises, for example two miniature display tubes 34 and 35. To this end, the stereoscopic image signal is applied to the display unit 33. The first miniature display tube 34 displays, with the given viewing direction, distance and magnification, the image data of the operating field for the user's left eye. Similarly, the second miniature display tube 35 displays the image data for the user's right eye in the same circumstances. Image data displayed on the display screens of the miniature display tubes are coupled into the operating microscope by means of a coupling device comprising coupling-in mirrors 37 and 38. The coupling-in mirrors can be moved between a deflected position, as denoted by dashed lines in the Figure, and an active position as denoted by solid lines. Via a selector switch 39, the user selects either the deflected position or the active position of the coupling-in mirrors. The display unit and the coupling-in mirrors constitute, together with the image processing unit 31, a display device for the visualization of image data of the operating field or also of a vicinity of the operating field. Via the binocular the user sees the operating field itself in alternation with the visualization of the image data of the same operating field or, if desired, of an area in a vicinity thereof. By alternating the positions of the coupling-in mirrors, the user of the operating microscope alternately observes the operating field itself and the processed image data of (a vicinity of) the operating field. When semi-transparent mirrors or tilting prisms are used for the coupling-in mirrors, the operating field can be observed simultaneously with the visualization of the image data. This enables comparison of the operating field observed with image data thereof. Instead of using movable mirrors or tilting prisms, use can also be made of stationary semi-transparent mirrors or stationary splitting prisms. The selector switch is then also suitable for switching the display unit on and off in order to enable observation of alternately the operating field alone or the operating field together with the reproduction of the image data.

When use is made of semi-transparent mirrors or splitting prisms, a part of the visualization provided by the display unit 33 is transmitted by the semi-transparent mirrors 37, 38 and a part of the image of the operating field itself is reflected so that it does not reach the exit of the binocular 3. A video camera 40 picks up the transmitted part of the visualization of the display unit and the reflected part of the image of the operating field itself and converts them into a video signal which is applied to a monitor 41. The monitor 41 then displays a composite image which is composed of the image of the operating field itself and of the visualization of three-dimensional image data. This composite image is the same as that of the operating field with simultaneous visualization by the display unit as viewed by the user of the operating microscope. Assistants of the user can then follow the progress of the operation on the monitor 41. If desired, the monitor 41 may also be arranged outside the operating room so that the operation can also be followed outside the operating room.

The processing of the image data includes, for example the accentuation of tumor tissue already detected by the imaging means. Recognition of the tumor tissue in the operating field is then facilitated by direct comparison with the image of the actual operating field. If desired, image data of a zone in the vicinity of the operating field can also be visualized, eventhough this zone in the actual operating field is (still) observed from view.

Via a control unit 36, the user can instruct the image processing unit to form a sectional plane through the image data and to process the image data in such a manner that the image data of structures present between the view point of user of the operating microscope and the selected sectional plane do not contribute to the stereoscopic image, thus creating an unobstructed view of the structures of interest in the image of the operating field and a vicinity thereof as produced by the image processing unit.

I claim:

1. An operating microscope for observing an operating field in an object, comprising an image display device for displaying an at least partly three dimensional image representation of an area of the object in the operating field derived from three dimensional image data of an internal structure of the object, and also comprising an optical system for combining the derived image representation with a spatial observation of the operating field in a manner that the derived at least partly three dimensional image representation is substantially spatially registered to the observation.

2. An operating microscope as claimed in claim 1, wherein the derived image representation constitutes a stereoscopic pair of images.

3. An operating microscope as claimed in claim 2, comprising a binocular with a left channel and a right channel, and means for reproducing a left image of the stereoscopic pair of images in the left channel and a right image of the stereoscopic pair of images in the right channel.

4. An operating microscope as claimed in claim 3, wherein the operating microscope has one or more variable settings from among viewing direction, distance and magnification of the operating field, and further comprises at least one position sensor for applying at least one electronic position signal to a converter for deriving each variable setting of the operating microscope and for applying an adjustment signal, corresponding to the setting, to an image processing unit for processing the image data for producing the derived image representation in conformity with the adjustment signal.

5. An operating microscope as claimed in claim 4, wherein said image processing unit is configured for forming a sectional plane through the image data and for processing the image data in a manner that portions of the object between a viewpoint of a user and the sectional plane do not contribute to the derived image representation.

6. An operating microscope as claimed in claim 5, wherein the operating microscope comprises an adjustable coupling device for selectively observing the operating field, the derived image representation or simultaneously a composite image of the operating field and the derived image representation.

7. An operating microscope as claimed in claim 6, wherein the coupling device comprises at least one movable mirror.

8. An operating microscope as claimed in claim 4, wherein the operating microscope comprises an adjustable coupling device for selectively observing the operating field, the derived image representation or simultaneously a composite image of the operating field and the derived image representation.

9. An operating microscope as claimed in claim 3, further comprising an image processing unit for producing the derived image representation, said image processing unit being configured for forming a sectional plane through the image data and for processing the image data in a manner that portions of the object between a viewpoint of a user and the sectional plane do not contribute to the derived image representation.

10. An operating microscope as claimed in claim 3, wherein the operating microscope comprises an adjustable coupling device for selectively observing the operating field, the derived image representation or simultaneously a composite image of the operating field and the derived image representation.

11. An operating microscope as claimed in claim 2, wherein the operating microscope has one or more variable settings from among viewing direction, distance and magnification of the operating field, and further comprises at least one position sensor for applying at least one electronic position signal to a converter for deriving each variable setting of the operating microscope and for applying an adjustment signal, corresponding to the setting, to an image processing unit for processing the image data for producing the derived image representation in conformity with the adjustment signal.

12. An operating microscope as claimed in claim 11, wherein said image processing unit is configured for forming a sectional plane through the image data and for processing the image data in a manner that portions of the object between a viewpoint of a user and the sectional plane do not contribute to the derived image representation.

13. An operating microscope as claimed in claim 11, wherein the operating microscope comprises an adjustable coupling device for selectively observing the operating field, the derived image representation or simultaneously a composite image of the operating field and the derived image representation.

14. An operating microscope as claimed in claim 2, further comprising an image processing unit for producing the derived image representation, said image processing unit being configured for forming a sectional plane through the image data.

15. An operating microscope as claimed in claim 2, wherein the operating microscope comprises an adjustable coupling device for selectively observing the operating field, the derived image representation or simultaneously a composite image of the operating field and the derived image representation.

16. An operating microscope as claimed in claim 1, wherein the operating microscope has one or more variable settings from among viewing direction, distance and magnification of the operating field, and further comprises at least one position sensor for applying at least one electronic position signal to a converter for deriving each variable setting of the operating microscope and for applying an adjustment signal, corresponding to the setting, to an image processing unit for processing the image data for producing the derived image representation in conformity with the adjustment signal.

17. An operating microscope as claimed in claim 16, wherein said image processing unit is configured for forming a sectional plane through the image data and for processing the image data in a manner that portions of the object between a viewpoint of a user and the sectional plane do not contribute to the derived image representation.

18. An operating microscope as claimed in claim 1, further comprising an image processing unit for producing the derived image representation, said image processing unit being configured for forming a sectional plane through the image data and for processing the image data in a manner that portions of the object between a viewpoint of a user and the sectional plane do not contribute to the derived image representation.

19. An operating microscope as claimed in claim 1, wherein the operating microscope comprises an adjustable coupling device for selectively observing the operating field, the derived image representation or simultaneously a composite image of the operating field and the derived image representation.

20. An operating microscope as claimed in claim 19, wherein the coupling device comprises at least one movable mirror.

* * * * *